(12) United States Patent
Kanngiesser

(10) Patent No.: US 6,429,664 B1
(45) Date of Patent: Aug. 6, 2002

(54) METHOD AND DEVICE FOR DETERMINING IN AN AEROSOL THE CONCENTRATION OF A MEDIUM WHICH IS DIFFERENT FROM AIR

(75) Inventor: Hartmut Kanngiesser, Zurich (CH)

(73) Assignee: SIG Combibloc GmbH, Linnich (DE)

( * ) Notice: Subject to any disclaimer, the term of this patent is extended or adjusted under 35 U.S.C. 154(b) by 0 days.

(21) Appl. No.: 09/319,813

(22) PCT Filed: Nov. 29, 1997

(86) PCT No.: PCT/EP97/06664

§ 371 (c)(1),
(2), (4) Date: Jul. 28, 1999

(87) PCT Pub. No.: WO98/26279

PCT Pub. Date: Jun. 18, 1998

(30) Foreign Application Priority Data

Dec. 11, 1996 (DE) .......................................... 196 51 490

(51) Int. Cl.[7] .............................................. G01R 27/04
(52) U.S. Cl. ...................................... 324/637; 324/640
(58) Field of Search ............................... 324/637, 636, 324/642, 647, 640, 632, 643, 639

(56) References Cited

U.S. PATENT DOCUMENTS

| 3,812,422 A | * | 5/1974 | De Corlis | 324/642 |
| 4,042,879 A | * | 8/1977 | Ho et al. | 324/636 |
| 4,567,749 A | | 2/1986 | Amblard et al. | 73/19 |
| 4,767,982 A | * | 8/1988 | Florig et al. | 324/640 |
| 5,656,774 A | * | 8/1997 | Nelson et al. | 73/290 |
| 5,898,308 A | * | 4/1999 | Champion | 324/643 |

FOREIGN PATENT DOCUMENTS

| DE | 3412704 A1 | 10/1984 |
| DE | 4211362 A1 | 10/1993 |
| DE | 4431001 A1 | 3/1995 |
| GB | 2110377 A | 8/1982 |

OTHER PUBLICATIONS

Ho, et al., "Microwave Measurement of the Liquid Water Content of Atmospheric Aerosols", Journal of Applied Meteorology, pp. 871–879, Dec. 1974.

Zhu, et al., "Microwave cavity spectrometer for process monitoring of ethylene oxide sterilization", pp. 103–108, Rev. Sci. Instrum., Vo. 64, No. 1, Jan. 1993.

Bakhtiari et al., "Microwave Swept–Frequency Optimization for Accurate Thickness of Dielectric Property Monitoring of Conductor–Backed Composites", pp. 740–743, Materials Evaluation, Jun. 1993.

Andresen, et al., "An automatic molecular beam microwave Fourier transform spectrometer", pp. 3694–3699, Rev. Sci. Instrum., vol. 61, No. 12, Dec. 1990.

Wittig, et al., "Untersucungen an Baustoffproben mit Mikrowellen", pp. 106–110, Materialprufung 33, 1991.

* cited by examiner

Primary Examiner—N. Le
Assistant Examiner—T. R. Sundaram
(74) Attorney, Agent, or Firm—Standley & Gilcrest LLP

(57) ABSTRACT

A method and device for determining the concentration of a medium other than air in an air/medium aerosol. The dielectric constant of the medium is measured using microwaves in a hollow conductor, with the aerosol passing through a neutral tube intersecting the hollow conductor. The microwave signal which propagates in the hollow conductor is subjected to attenuation and a phase shift due to the difference between the dielectric constant of the medium and that of air, the phase shift of the microwave signal being measured by taking into account the active path length (the tube in the cross section of the hollow conductor).

12 Claims, 4 Drawing Sheets

Block Diagram

Wiring Diagram

METHOD AND DEVICE FOR DETERMINING IN AN AEROSOL THE CONCENTRATION OF A MEDIUM WHICH IS DIFFERENT FROM AIR

BACKGROUND AND SUMMARY OF THE INVENTION

This invention concerns a method and a device for determining the concentration of a medium other than air in an air/medium aerosol. The dielectric constant of the medium is measured using microwaves in a hollow conductor, with the aerosol passing through a neutral tube intersecting the hollow conductor. The microwave signal which propagates in the hollow conductor is subjected to attenuation and a phase shift due to the difference between the dielectric constant of the medium and that of air, the phase shift of the microwave signal being measured by taking into account the active path length (the tube in the cross section of the hollow conductor).

When determination of the $H_2O_2$ concentration is mentioned in the present patent application, it is not intended to restrict the scope in any way, but instead is given merely as an example of determining the concentration of a medium in an air/medium aerosol.

In packaging installations for aseptic packaging of foodstuffs in laminated packages, the packages are sterilized by introducing a hot air/$H_2O_2$ aerosol immediately before they are filled. This aerosol is prepared by a metering system in which the concentration of an $H_2O_2$ solution ($H_2O_2$ in water) is adjusted in a stream of air. To achieve optimal sterilization under economical conditions, it is important to measure the $H_2O_2$ concentration in the aerosol. Finally, the total quantity of $H_2O_2$ used is determined from the quantity of air used and the $H_2O_2$ concentration.

Although the quantity of air in a metering system is measured by means of suspended solid particles and then can be kept constant by adjusting the air pressure, the $H_2O_2$ concentration must be calculated. It is possible here to use measurement methods in which the measured quantity depends on the volume of $H_2O_2$, or to use measurement methods in which the measured quantity depends on the $H_2O_2$ droplet count in the aerosol.

Measurement methods based on volume have the advantage that they yield the desired measurement results directly and without conversion. In addition, a measurement method is to be provided that is capable of performing measurements by using the connecting tubes which are present anyway, without requiring direct contact with the measurement instrument and the medium—for example, $H_2O_2$ which is highly corrosive. A measurement of the dielectric constant which differs from that in air is to be considered for this purpose.

It is known from W. Ho et al.: "Microwave measurements of the liquid water content of atmospheric aerosols," Journal of Applied Meteorology, vol. 13, no. 8, 1974, USA, pages 871–879, XP002058849, that the amount of liquid water in atmospheric aerosols can be measured with the help of microwave measurements. The background of these measurements is studies of the influence of the relative atmospheric humidity on the range of vision, in a fog, for example. With the known device, liquid particles are filtered by a filter out of gas passed through a pipeline and collected. This filter for liquid particles is located at the center of a cavity resonator whose resonant frequency is shifted by the presence of material having a high dielectric constant in the filter. The change in frequency in the cavity resonator is used as a measure of the concentration of the aerosol.

It is a problem with the device known from the state of the art that the concentration of the aerosol can be measured only as a semi-continuous measurement, because the filter must be dried regularly to correct for fluctuations in ambient influences. Another problem with the known device is that the only variations in concentration that can be detected with it over time are those having a time constant much greater than the time of the drying cycles of the filters. Typical intervals of approximately 20 minutes are mentioned in the state of the art. This is by far insufficient for controlling concentrations in packaging facilities, such as for aseptic packaging, for example.

German Patent No. 4,431,001 A1 discloses a method and a device for measuring the dielectric constant with a hollow conductor and a microwave transmitter and receiver. The hollow conductor is designed as a cavity resonator, having a transverse slit in its central area to arrange a test page perpendicular to the longitudinal direction of the hollow conductor. The dielectric constant of the specimen can be measured by the difference between the resonant frequencies of the cavity resonator, with and without the specimen.

The object of this invention is to design and improve upon the known device and the known method of measuring the concentration of an air/water aerosol, so they can be used with little complexity in terms of measurement technology to measure the concentration of a medium other than air in an aerosol flowing through the hollow conductor.

This objective is characterized according to this method by the fact that there is equalization to the phase shift of an aerosol with a known dielectric constant, and an average is formed from the concentration values thus determined. By reflecting the microwave signal at a short circuit in the hollow conductor, a standing wave is generated with a maximum electric field in the area of the tube, and the geometric and electric configurations are adjusted so that the phase shift is directly proportional to the concentration of the medium.

In terms of equipment, this object is achieved with a sensor and an analyzing unit. The sensor is formed by a hollow conductor, a microwave transmitter, and a microwave receiver, and has a neutral tube passing through the hollow conductor to carry the aerosol due to the fact that the microwave transmitter and receiver are arranged in the hollow conductor. One end of the hollow conductor is closed by a longitudinally displaceable, electrically conducting short circuit, and the tube is arranged in the maximum electric field of the standing wave generated in the hollow conductor. The analyzing unit has at least one preamplifier for voltage balancing and two low-pass filters for measuring the fluctuations in the concentration ($W_a$) of the medium and the average ($W_m$) concentration of the medium.

With the method according to this invention, a microwave signal propagates in the hollow conductor within which there is a tube with a flowing aerosol. The signal is scattered by the transitions from air to droplets and back, yielding attenuation in the direction of propagation of the wave. On the other hand, due to the presence of droplets having a different dielectric constant, there is a shift in transit time which can be measured from the outside as a phase shift at a constant operating frequency.

It has been found that the phase measurements and absorption measurement follow qualitatively the same pattern, so it is possible to use the measurement with the higher signal yield, the phase shift, or a combination of phase shift and absorption measurement. This leads to reduced complexity in terms of measurement technology because phase and amplitude need not be measured separately, and therefore the signal curves in the working frequency range need not be analyzed. Due to the identity of phase and amplitude curves, the relative measurement is sufficient, and there is no harm in mixing the amplitude measurement and phase measurement.

As with the state of the art previously cited, it is possible to arrange the microwave transmitter at one end of the hollow conductor and the receiver at the other end. However, in a preferred embodiment of the invention, both the microwave transmitter and the receiver are arranged at one end of the hollow conductor, and the other end of the hollow conductor is sealed by an electrically conducting short circuit. This short circuit is an electrically conducting element that fills up the entire hollow cross-section of the hollow conductor and reflects the measurement distance, so that a standing wave is formed in the hollow conductor and is altered by the aerosol. The hollow conductor preferably has a rectangular cross section, and the tube preferably runs across the longitudinal direction of the hollow conductor. In a preferred embodiment of the invention, the tube is arranged at the maximum of the electric field of the standing wave formed in the hollow conductor.

To standardize the aerosol flow conditions in the tube passing through the hollow conductor, a preferred embodiment of this invention provides for the tube to have a 180° curvature immediately before its entrance into the hollow conductor, and for it to run preferably in a curved pipe. In this way, the sensitivity of the device over the cross-section of the tube can be standardized.

An especially simple design in terms of measurement technology is achieved according to this invention by using a conventional motion sensor as the microwave transmitter and receiver. Such motion sensors include both a microwave source and a mixer diode, whose output signals are already in the baseband. In addition, such motion sensors, which already have a flange for connecting to a hollow conductor, are currently commercially available.

An oscilloscope can be used to display the fluctuations in aerosol concentration and the average aerosol concentration, and a multimeter can be used for displaying the average alone.

BRIEF DESCRIPTION OF THE DRAWINGS

The exact functioning of the method according to this invention and the corresponding device are explained in greater detail below on the basis of drawings illustrating a preferred embodiment, wherein.

DETAILED DESCRIPTION OF THE PREFERRED EMBODIMENT(S)

Figure 1:
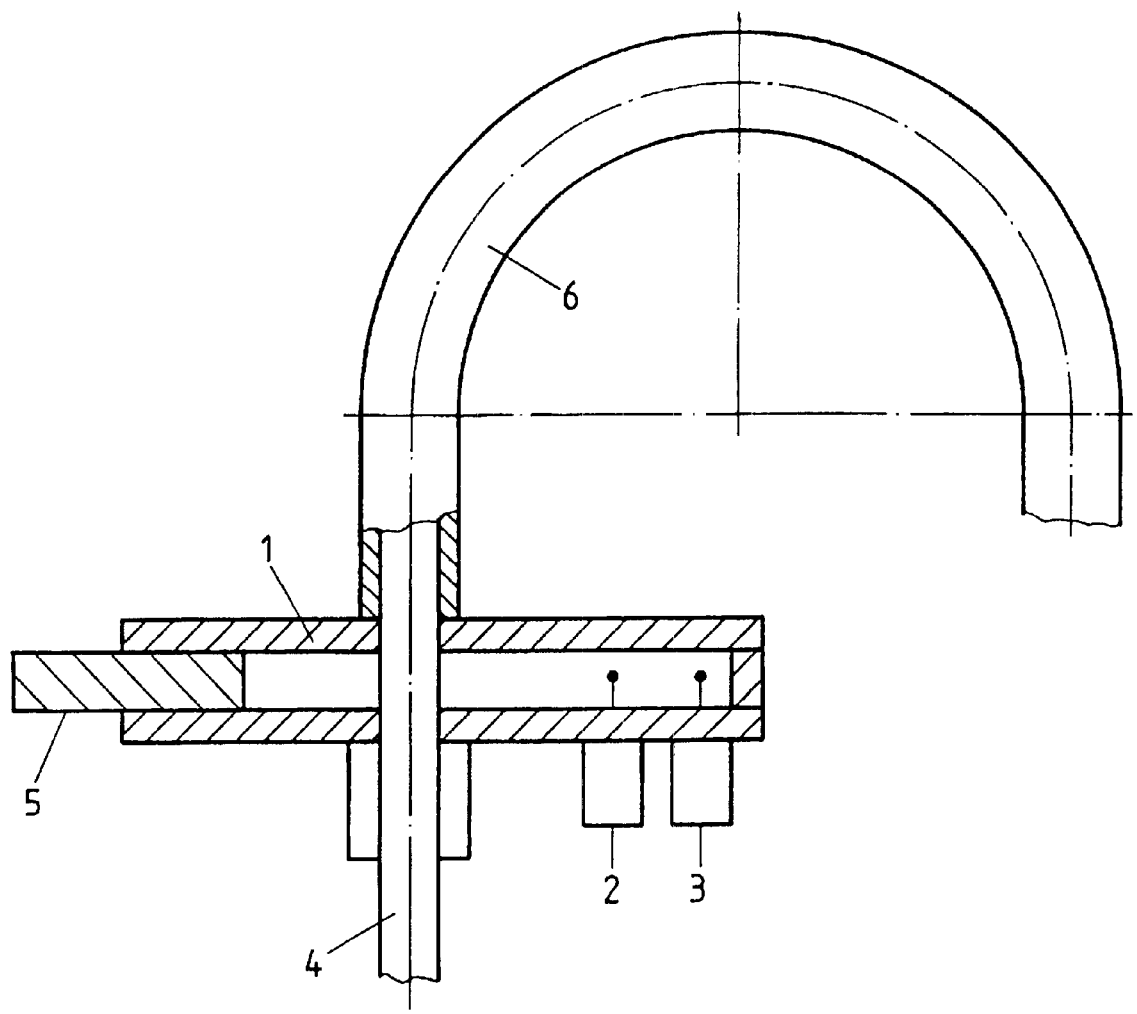
FIG. 1 depicts the sensor of the device according to a preferred embodiment of the present invention, schematically in a longitudinal section.

FIG. 1 shows a schematic view of the sensor of the device in a preferred embodiment of the present invention. The sensor, shown in longitudinal section, has a hollow conductor 1 of preferably rectangular cross section, with a microwave transmitter 2 and a microwave receiver 3 arranged at one end thereof. A tube 4, preferably made of plastic, for conducting the aerosol through the hollow conductor 1 is arranged crosswise through the hollow conductor 1. The other end of hollow conductor 1 is filled by an electrically conducting short circuit 5 which fills up the entire inside cross section of the hollow conductor 1. The short circuit 5 is arranged so that it is longitudinally displaceable in the hollow conductor 1 and it is extracted from the hollow conductor 1 at constant increments to determine the best operating point, which corresponds to increasing the concentration of the medium to be measured. It has been found that the range of increasing detector voltages is approximately linear. The zero point to be established by the displaceable short circuit 5 should preferably be positioned shortly after the maximum negative detector voltage is exceeded.

To achieve a maximum effect of the aerosol on the phase shift displacement, the tube 4 is preferably arranged at the maximum of the electric field of the standing wave formed in hollow conductor 1.

During measurement, it has been found that the output voltage of the sensor shows a strong dependence on the position of the tube 4 and its curvature before entering the hollow conductor 1. This effect is based on the fact that the sensitivity is not constant over the cross-section of the tube 4. Instead, the output voltage is influenced by the distribution of the aerosol concentration over the cross section of the tube 4. In a preferred embodiment of the sensor of the device which is shown in FIG. 1, the dependence on the position and curvature of the tube 4 outside of hollow conductor 1 could be eliminated by a fixed 180° curvature of the tube 4, running in a curved pipe 6 before the point of entrance into the hollow conductor 1.

Figure 2:
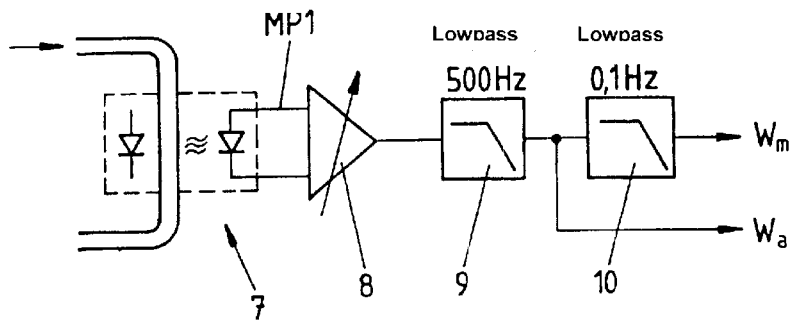
FIG. 2 is a wiring diagram and a block diagram of the analyzing unit of the device according to a preferred embodiment of the present invention.
Figure 2:
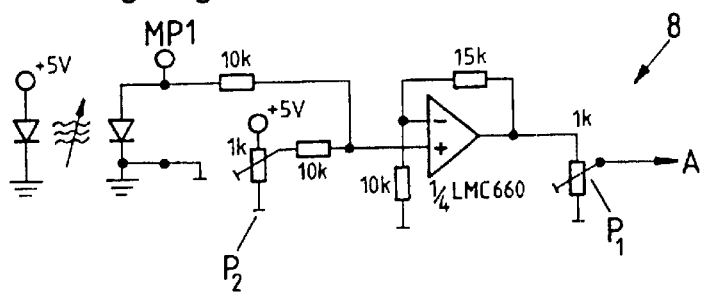
Figure 2:
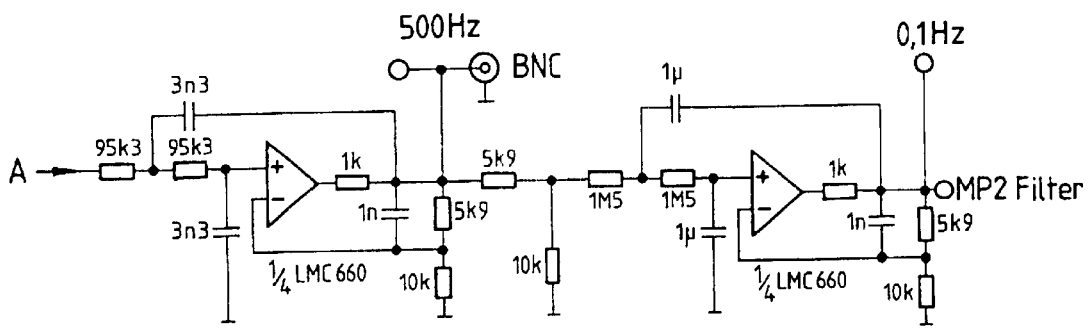
Figure 2:
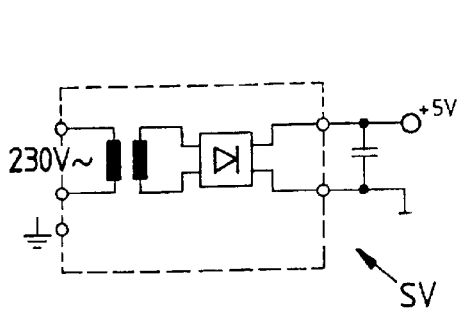

Next, FIG. 2 shows a block diagram and wiring diagram for a preferred embodiment of the analyzing unit of the device according to the present invention. The sensor 7, which is described in greater detail with reference to FIG. 1, is shown only schematically in the block diagram. Voltages picked off at the mixer diode of the microwave receiver 3 (FIG. 1) are between −1 V and −2 V, depending on design. With an increase in the concentration of the medium, the negative voltages become lower. Therefore, to obtain the concentration directly as a voltage signal, the output voltage must be shifted by the zero point value. To this extent, the analyzing unit has a potentiometer $P_1$ in the preamplifier 8.

Finally, the block diagram also shows that the analyzing unit has two low-pass filters 9, 10. In measuring the $H_2O_2$ concentration in an air/$H_2O_2$ aerosol, the corner frequency of one low-pass filter 9 should be approximately 500 Hz and that of the other low-pass filter 10 should be approximately 0.1 Hz. Thus, the voltage of the concentration of aerosol in the tube can be measured at the output of low-pass filter 9, and the average ($W_m$) of the concentration can be read at the output of low-pass filter 10. The low-pass filters 9, 10 preferably have Butterworth characteristics to guarantee rapid stabilization with a slight overshoot in the output signals.

The electronic system of the analyzing unit voltage supply works with a power supply SV. A power supply that permits only positive output voltages should be selected. The output signals are preferably at +1 V with respect to chassis ground so that negative shifts in zero point can also be detected.

Figure 3:
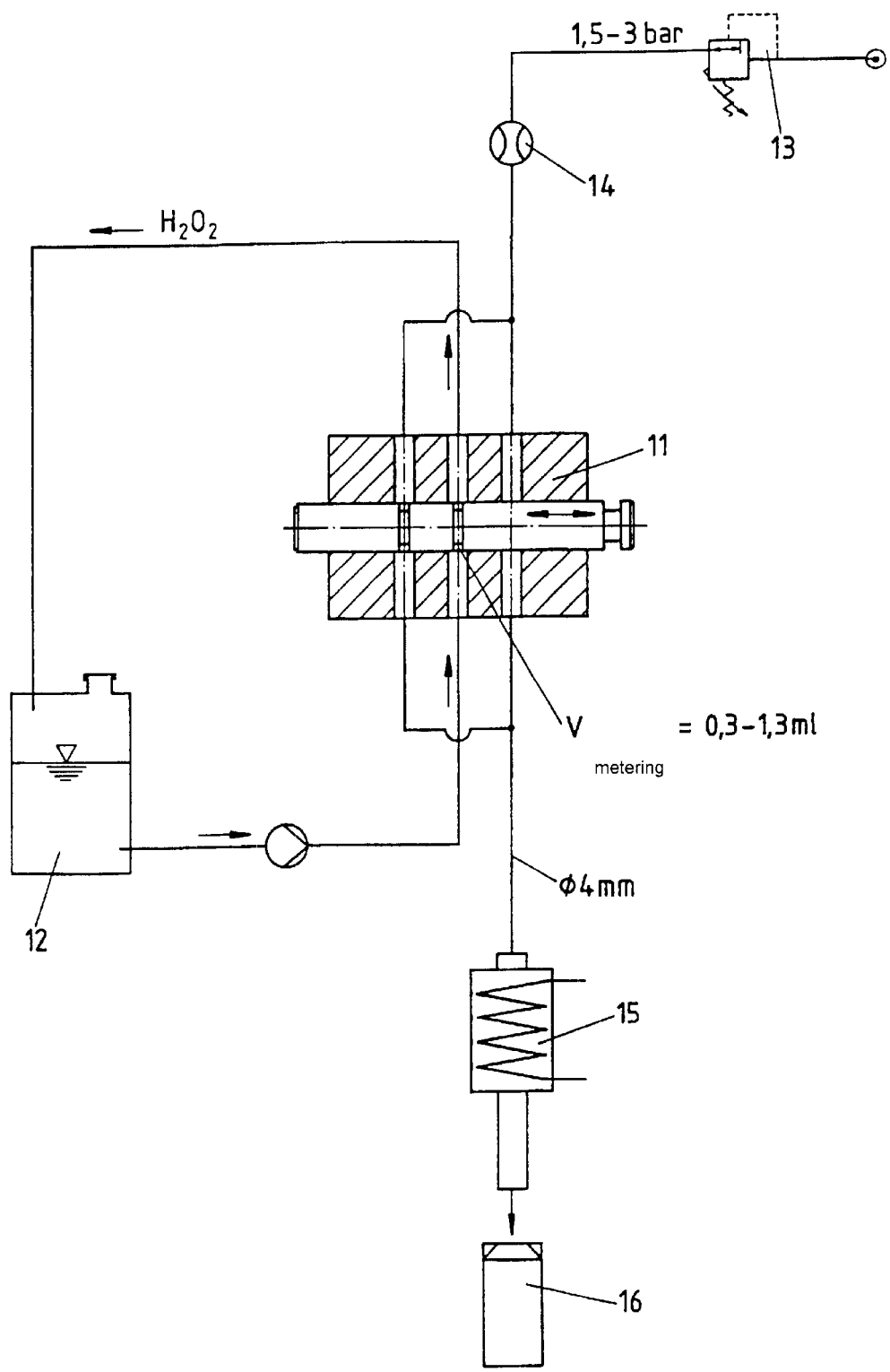
FIG. 3 is a schematic diagram of the metering system to be equipped with the device according to a preferred embodiment of the present invention.

As already mentioned, the $H_2O_2$ concentration in an air/$H_2O_2$ aerosol in a metering system is to be measured in a preferred embodiment of the invention. Such a metering system is shown as a schematic diagram in FIG. 3. Metering takes place within a piston metering device 11, which is connected to a tank 12 for supplying the $H_2O_2$ by means of inlet and return lines (not shown). The compressed air, which is provided by a compressor 13, is measured in an air flow meter 14 and sent to piston metering device 11. Turbulence is generated in the entire metering system and in the connecting lines, thus forming the air/$H_2O_2$ aerosol. This aerosol first passes by a heater 15 and then enters an empty package 16, which it thereby sterilizes.

Figure 4:
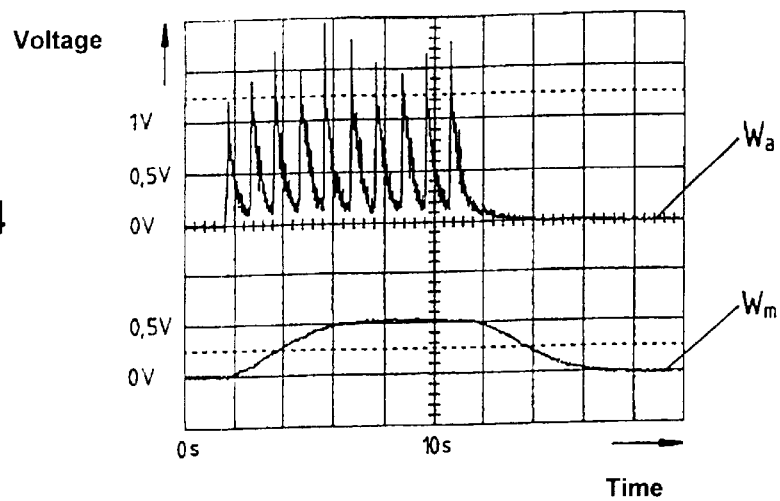
FIG. 4 shows a graph of output voltage over time for a preferred embodiment of the present invention, with a on metering device operating at one stroke per second.

FIG. 4 shows a graph of output voltage over time. The upper voltage curve shows the concentration fluctuations of the instantaneous value ($W_a$), measured at the output of the 500 Hz low-pass filter 9, while the lower voltage curve is measured at the output of the 0.1 Hz low-pass filter 10, showing the average value ($W_m$) of the measured voltage. The graph of FIG. 4 represents results obtained with a piston metering device 11 operating at one stroke per second. In this example, the outputs of the measurement device are calibrated to 1 V/mL water in the aerosol. The piston metering device 11 delivers approximately 0.5 mL water per stroke in an airstream of approximately 3.5 m$^3$ [STP]/h. Averaged over time, this yields a water flow rate of approximately 30 mL/min at one stroke per second.

Figure 5:
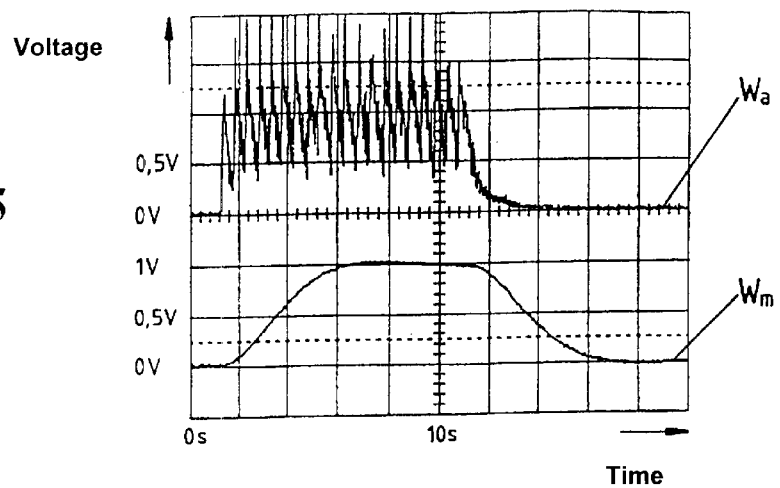
FIG. 5 also shows a graph of output voltage over time for a preferred embodiment of the present invention, but with the piston metering device operating at two strokes per second.

FIG. 5 is also a graph of output voltage over time, as in FIG. 4, but with the piston metering device 11 operating at two strokes per second. Consequently, the average value ($W_m$) of the measured voltage, is also twice as great as in the measurement in FIG. 4.

Figure 6:
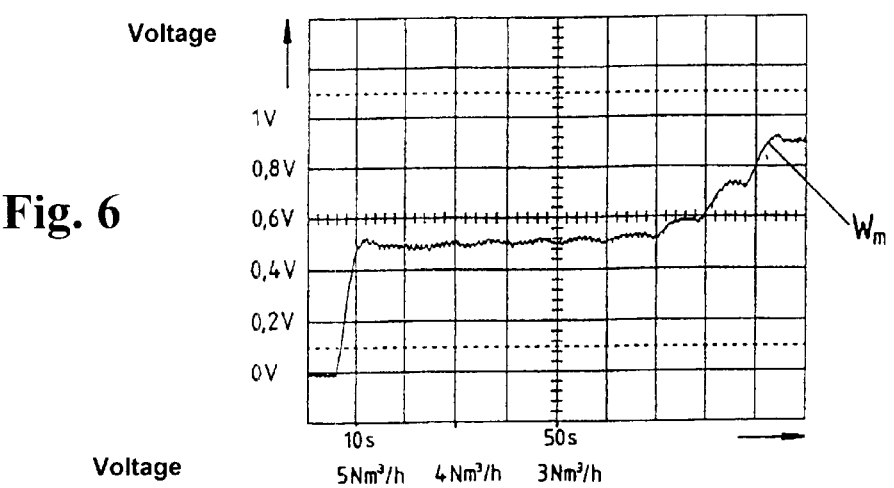
FIG. 6 shows a graph of output voltage vs. air flow rate for a preferred embodiment of the present invention.

Finally, FIG. 6 shows that the display of the device according to this invention is virtually independent of the air flow rate. The voltage curve shown in FIG. 6 was picked off at the output of the 0.1 Hz low-pass filter 10. An air flow rate of 5 m$^3$ [STP]/h after 10 seconds was used and was reduced by 0.5 m$^3$ [STP] per hour every 10 seconds. The measurements ended at 1 m$^3$ [STP]/h.

For compensation of the device according to a preferred embodiment of the invention, first the voltage at the mixer diode of microwave receiver 3 must be adjusted with the longitudinally displaceable short circuit 5 for the maximum negative voltage with respect to chassis ground, while the piston metering device 11 is switched off.

In addition, with the piston metering device 11 shut down, the voltage at the output of the low-pass filter 10 must be set at 0 V with the potentiometer $P_1$. Then, with the piston metering device 11 running, a measurement is performed with the potentiometer $P_1$ of the preamplifier 8, with the measurement point of the output of the 0.1 Hz lowpass filter 10 set at 0.5 V with respect to chassis ground. Finally, with piston metering device 11 switched off again, the voltage at the output of the 0.1 Hz low-pass filter 10, now measured against +1 V with respect to chassis ground, is adjusted from −1 V to 0 V with the potentiometer $P_1$, of the preamplifier 8. Thus, adjustment of the device according to a preferred embodiment of the invention is concluded, and the measurement instrument is ready for use.

The scope of the invention is not to be considered limited by the above disclosure, and modifications are possible without departing from the spirit of the invention as evidenced by the following claims.

What is claimed is:

1. A method of determining the concentration of a medium other than air in an air/medium aerosol by measuring the dielectric constant of the medium using microwaves in a hollow conductor, said method comprising the steps of;

passing the aerosol through the hollow conductor via an intersecting, neutral tube, the neutral tube having a substantially 180° curvature immediately prior to entering the conductor;

providing a microwave source and microwave receiver at a first end of the hollow conductor;

providing a short circuit at a second end of the hollow conductor so that the neutral tube lies between the short circuit and the microwave source and receiver, the short circuit being longitudinally displaceable within the hollow conductor to allow for an optimal operating point to be obtained;

providing an analyzing unit having first and second low pass filters, and at least one preamplifier that is in electronic communication with a potentiometer;

generating a standing wave within the hollow conductor that has a maximum electric field in the area of the neutral tube by reflecting a microwave signal from the microwave source on the short circuit;

measuring the phase shift of the microwave signal, taking into account the active path length (the tube in the cross section of the hollow conductor), wherein an adjustment to the phase shift of an aerosol having a known dielectric constant is performed;

adjusting the geometric and electric configurations so that the phase shift is directly proportional to the concentration of the medium; and forming an average from the concentration values of the medium thus determined;

whereby the voltage representing the instantaneous concentration of the aerosol in the tube is read at the first low pass filter of the analyzing unit, and the voltage representing the average concentration of the aerosol is read at the second low pass filter of the analyzing unit.

2. The method of claim 1, further comprising providing an oscilloscope for displaying the concentration fluctuations of the aerosol and the average aerosol concentration.

3. The method of claim 1, further comprising providing a multimeter for displaying the average aerosol concentration.

4. A device for determining the concentration of a medium other than air in an aerosol, in particular, the $H_2O_2$ concentration in an air/$H_2O_2$ aerosol, said device comprising:

a sensor formed by a hollow conductor, a microwave transmitter and receiver, and a longitudinally displaceable, electronically conducting short circuit;

an analyzing unit having at least one preamplifier for voltage compensation, and two low-pass filters for measuring the fluctuations in concentration of the medium and the average concentration of the medium; and a neutral tube passing through the hollow conductor for flow-through of the aerosol, the neutral tube having a substantially 180° curvature immediately prior to entering the hollow conductor;

wherein the microwave transmitter and receiver are arranged at one end of the hollow conductor, the other end of the hollow conductor is closed by the longitudinally displaceable, electrically conducting short circuit, and the neutral tube is arranged in the maximum electric field of a standing wave generated in the hollow conductor.

5. A device according to claim 4, wherein the hollow conductor has a rectangular cross section.

6. A device according to claim 4, wherein the tube runs across the longitudinal direction of the hollow conductor.

7. A device according to claim 4, wherein the tube is passed through a curved pipe to achieve the curvature.

8. A device according to claim 7, wherein the sensor, the curved pipe, the analyzing unit, and a power supply are arranged in a housing.

9. A device according to claim 4, wherein a conventional commercial motion sensor is used as the microwave transmitter and the microwave receiver.

10. A device according to claim 4, wherein an oscilloscope is used to display the concentration fluctuations of the aerosol and the average aerosol concentration.

11. A device according to claim 4, wherein a multimeter is used to display the average aerosol concentration.

12. A method of determining the concentration of a medium other than air in an air/medium aerosol by measuring the dielectric constant of the medium using microwaves in a hollow conductor, said method comprising the steps of;

passing the aerosol through the hollow conductor via an intersecting, neutral tube, the neutral tube having a substantially 180° curvature immediately prior to entering the conductor;

providing a microwave source and microwave receiver at a first end of the hollow conductor;

providing a longitudinally displaceable short circuit at a second end of the hollow conductor to reflect microwave signals from the microwave source;

generating a standing wave within the hollow conductor by reflecting a microwave signal from the microwave source on the short circuit;

measuring the phase shift of the microwave signal, taking into account the active path length (the tube in the cross section of the hollow conductor), wherein an adjustment to the phase shift of an aerosol having a known dielectric constant is performed;

adjusting the geometric and electric configurations so that the phase shift is directly proportional to the concentration of the medium; and forming an average from the concentration values of the medium thus determined.

* * * * *